(12) United States Patent
Kim

(10) Patent No.: US 10,596,016 B2
(45) Date of Patent: Mar. 24, 2020

(54) ENDOVASCULAR DEVICE CONFIGURED FOR SEQUENCED SHAPE MEMORY DEPLOYMENT IN A BODY VESSEL

(71) Applicant: Cook Medical Technologies LLC, Bloomington, IN (US)

(72) Inventor: Woong Kim, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 10 days.

(21) Appl. No.: 15/699,442

(22) Filed: Sep. 8, 2017

(65) Prior Publication Data

US 2019/0076275 A1    Mar. 14, 2019

(51) Int. Cl.
*A61F 2/82* (2013.01)
*A61F 2/88* (2006.01)
*A61L 31/02* (2006.01)
*A61L 31/14* (2006.01)

(52) U.S. Cl.
CPC .............. *A61F 2/88* (2013.01); *A61L 31/022* (2013.01); *A61L 31/14* (2013.01); *A61F 2210/0023* (2013.01); *A61F 2210/0071* (2013.01); *A61F 2230/0069* (2013.01); *A61F 2240/001* (2013.01); *A61F 2250/0042* (2013.01); *A61F 2310/00011* (2013.01); *A61L 2400/16* (2013.01)

(58) Field of Classification Search
CPC ....................................................... A61F 2/82
See application file for complete search history.

(56) References Cited

U.S. PATENT DOCUMENTS

| | | | |
|---|---|---|---|
| 5,025,799 | A | 6/1991 | Wilson |
| 5,466,242 | A | 11/1995 | Mori |
| 5,601,593 | A | 2/1997 | Freitag |
| 5,882,444 | A | 3/1999 | Flomenblit et al. |
| 6,080,160 | A | 6/2000 | Chen et al. |
| 6,238,421 | B1 | 5/2001 | Günther et al. |
| 9,186,853 | B2 | 11/2015 | Khan et al. |

(Continued)

FOREIGN PATENT DOCUMENTS

| | | |
|---|---|---|
| EP | 0 666 065 A1 | 8/1995 |
| EP | 0 730 848 A2 | 9/1996 |
| WO | WO 2016008043 A1 | 1/2016 |

OTHER PUBLICATIONS

Drexel, Masao J. et al., "The Effects of Cold Work and Heat Treatment on the Properties of Nitinol Wire," Proceedings of the International Conference on Shape Memory and Superelastic Technologies, SMST-2006, Pacific Grove, CA, pp. 447-454.

(Continued)

*Primary Examiner* — Matthew W Schall
(74) *Attorney, Agent, or Firm* — Brinks Gilson & Lione

(57) ABSTRACT

A method of sequenced deployment of an endovascular device comprises delivering, into a body vessel, a Nitinol structural element comprising n deployable regions each having a local austenite finish temperature above body temperature. The local austenite finish temperature of at least one of the n deployable regions is different from the local austenite finish temperature of another of the n deployable regions. During and/or after delivery, the Nitinol structural element is heated above body temperature, and each of the n deployable regions is deployed when the local austenite finish temperature thereof is reached. Thus, a deployed configuration of an endovascular device is achieved in a sequenced deployment process.

15 Claims, 2 Drawing Sheets

(56) References Cited

U.S. PATENT DOCUMENTS

| | | |
|---|---|---|
| 9,675,481 B2 | 6/2017 | Vad |
| 2006/0064055 A1 | 3/2006 | Pile-Spellman et al. |
| 2006/0206140 A1 | 9/2006 | Shaolian et al. |
| 2007/0073380 A1 | 3/2007 | Vazquez et al. |
| 2008/0319525 A1 | 12/2008 | Tieu et al. |
| 2009/0054918 A1 | 2/2009 | Henson |
| 2009/0088838 A1 | 4/2009 | Shaolian et al. |
| 2014/0207109 A1 | 7/2014 | Laramy et al. |
| 2015/0072299 A1 | 3/2015 | Alauddin et al. |
| 2015/0369223 A1 | 12/2015 | Hallila et al. |
| 2016/0287354 A1 | 10/2016 | Viecilli et al. |

OTHER PUBLICATIONS

Drexel, Masao J. et al., "The Effects of Cold Work and Heat Treatment on the Properties of Nitinol Wire," ASME 2007, 2nd Frontiers in Biomedical Devices Conference; Paper No. BioMed2007-38012, Irvine, CA. pp. 89-90.

Fei, Xueling et al., "Surface form memory in NiTi shape memory alloys by laser shock indentation," *Journal of Materials Science*, 47, 5 (2012) pp. 2088-2094.

Müller, Christian W. et al., "Electromagnetic Induction Heating of an Orthopaedic Nickel-Titanium Shape Memory Device," *Journal of Orthopaedic Research*, 12, (2010), pp. 1671-1676.

Pfeifer, Ronny et al., "Adaptable Orthopedic Shape Memory Implants," *Procedia CIRP*, 5 (2013) pp. 253-258.

European Search Report from corresponding EP Application No. 18275129.7, dated Feb. 5, 2019, 8p.

Karamichailidou, Socrates Xenos-Despina; "The Unique Properties, Manufacturing Processes and Applications of Near Equatomic Ni—Ti Alloys"; Jan. 15, 2016, pp. 1-35; University of Thessaly, Department of Mechanical Engineering Laboratory of Materials; Thessaly, Greece.

ENDOVASCULAR DEVICE CONFIGURED FOR SEQUENCED SHAPE MEMORY DEPLOYMENT IN A BODY VESSEL

TECHNICAL FIELD

The present disclosure is related generally to endovascular devices and more specifically to an endovascular device comprising a nickel-titanium shape memory alloy ("Nitinol").

BACKGROUND

Superelastic deployment of Nitinol-based endovascular devices is widely used to implant stents, filters and other devices into blood vessels. Such devices are typically heat set to a single static shape (e.g., a radially expanded shape in the case of a stent) that can be recovered spontaneously upon removal of a constraining force, such as an overlying tubular sheath, after delivery of the device into a target vessel. Such nitinol-based devices may have austenite finish temperatures ($A_f$) below body temperature to ensure that removal of the constraining force, once the device is delivered into the vessel, is sufficient to induce the transformation from martensite to austenite that is needed for shape recovery. Shape memory deployment of endovascular devices, where austenite finish temperatures may be at or above body temperature and heating is employed to induce shape recovery, is not widely used for Nitinol-based endovascular devices due to a number of practical challenges, such as the difficulty of controlling temperature in situ. Furthermore, current Nitinol-based endovascular devices utilize a bimodal approach of deformation and recovery to a preset shape defined by a single $A_f$ temperature.

BRIEF SUMMARY

An endovascular device configured for sequenced deployment in a body vessel comprises a Nitinol structural element having n deployable regions, where n is an integer greater than 1 and where each of the n deployable regions comprises a local austenite finish temperature above body temperature. The local austenite finish temperature of at least one of the n deployable regions is different from the local austenite finish temperature of another of the n deployable regions, and thus the endovascular device is configured for sequenced deployment within a body vessel.

A method of sequenced deployment of an endovascular device comprises delivering, into a body vessel, a Nitinol structural element comprising n deployable regions each having a local austenite finish temperature above body temperature. The local austenite finish temperature of at least one of the n deployable regions is different from the local austenite finish temperature of another of the n deployable regions. The Nitinol structural element is heated above body temperature, during and/or after delivery into the body vessel, and each of the n deployable regions is deployed when the local austenite finish temperature thereof is reached. Thus, a deployed configuration of an endovascular device is achieved in a sequenced deployment process.

A method of heat setting an endovascular device for sequenced deployment in a body vessel includes securing a Nitinol structural element in a predetermined configuration, and selectively heating each of n discrete regions of the Nitinol structural element. The selective heating occurs under conditions sufficient to induce the Nitinol structural element to adopt a local austenite finish temperature above body temperature in each of the n discrete regions. After the selective heating, the local austenite finish temperature of at least one of the n discrete regions is different from the local austenite finish temperature of another of the n discrete regions, which serve as n deployable regions configured for sequenced deployment within a body vessel.

DETAILED DESCRIPTION

The present disclosure describes a "smart" self-deploying endovascular device that can be deployed in a sequenced manner, where different regions of the device are deployed at different times while the device is heated, preferably by a remote heat source. The method is enabled by the use of a Nitinol structural element having predetermined local variations in phase transformation temperature (e.g., austenite finish temperature, or $A_f$). The Nitinol structural element may take the form of a wire or another shape, such as a rod, tube or strip, preferably having an elongated geometry. The endovascular device may be readily delivered in an undeployed configuration to a treatment site and then deployed in a sequential process activated by temperature to a simple or complex shape.

The Nitinol structural element comprises a nickel-titanium alloy that exhibits shape memory behavior. In other words, the nickel-titanium alloy can undergo a phase transformation that allows it to "remember" and return to a previous shape or configuration. More specifically, the nickel-titanium alloy can transform between a lower temperature phase (e.g., martensite) and a higher temperature phase (e.g., austenite) in order to effect shape or strain recovery. As would be known by the skilled artisan, austenite is characteristically the stronger phase, and martensite may be deformed up to a recoverable strain of about 8%. Strain introduced in the alloy in the martensitic phase may be substantially recovered upon completion of a reverse phase transformation to austenite, allowing the alloy to return to the previous shape. The temperature at which the strain recovery occurs may depend on the phase transformation temperatures of the nickel-titanium alloy, as discussed further below. The strain recovery can be driven by the application and removal of stress (superelastic effect) and/or by a change in temperature (shape memory effect), as in the present disclosure. Such alloys are commonly referred to as Nitinol or Nitinol alloys, and they are typically near-equiatomic in composition.

Figure 1:
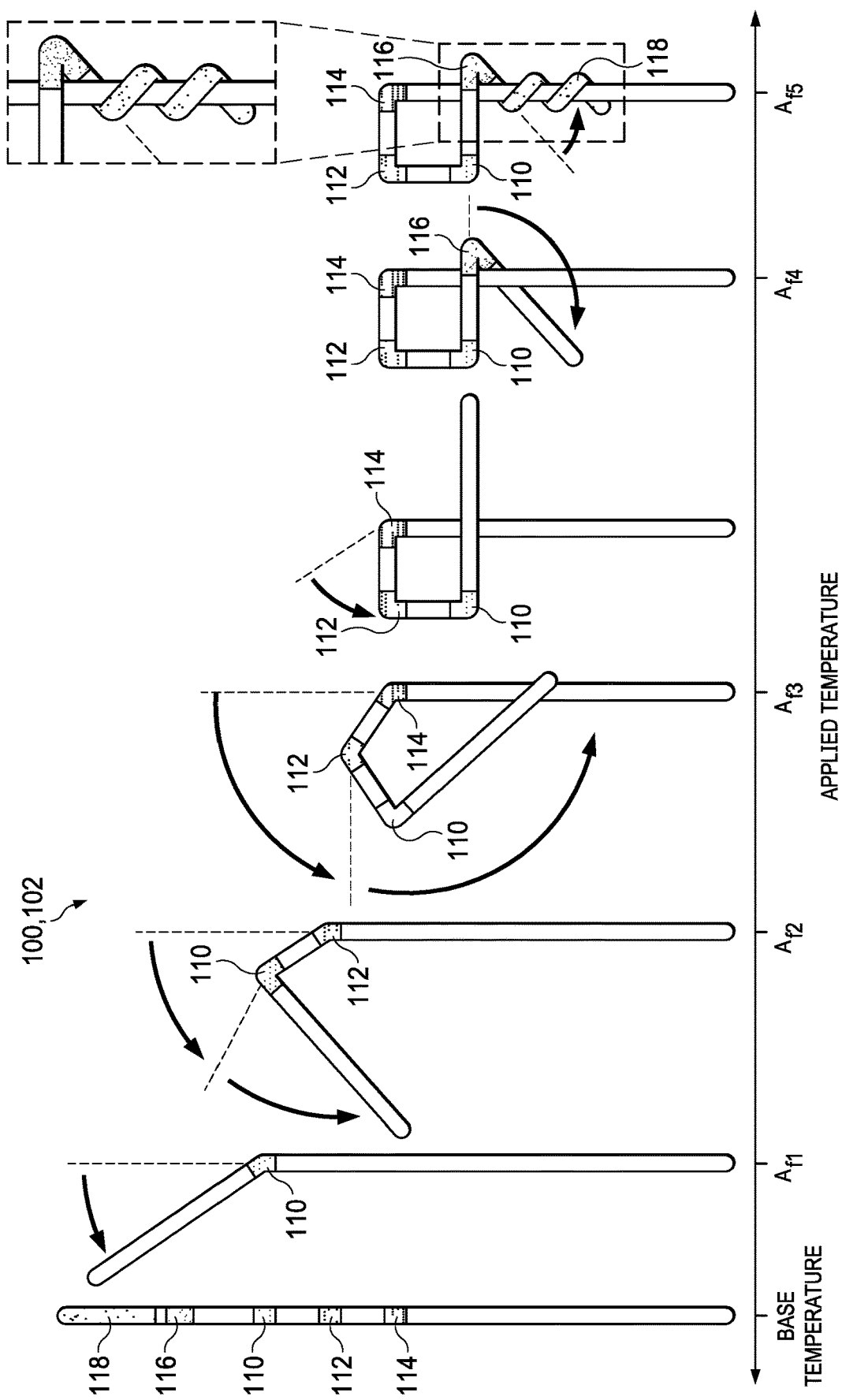
FIG. 1 includes a series of schematics showing sequenced deployment of an exemplary endovascular device comprising a Nitinol structural element as a function of temperature. The Nitinol structural element of this example has n=5 deployable regions, each with a different local austenite finish temperature.

The method may be understood in view of the schematics of FIG. 1, which provide an example of the sequenced deployment of an exemplary endovascular device 100 comprising a Nitinol structural element 102. The endovascular device 100 is shown in the left-hand side of FIG. 1 in a delivery (or undeployed) configuration, and on the right-hand side of FIG. 1 in a fully deployed configuration. In between, the endovascular device 100 is shown undergoing sequenced deployment, where discrete regions of the Nitinol structural element 102 exhibit shape recovery at different times as a function of temperature. Each discrete region (or "deployable region") may be isolated from or directly adjacent to another deployable region.

The Nitinol structural element 102 of this example includes five deployable regions 110,112,114,116,118 each having a local austenite finish temperature above body temperature. In this example, all of the local austenite finish temperatures (denoted as $A_{f1}$, $A_{f2}$, $A_{f3}$, $A_{f4}$ and $A_{f5}$ for the first, second, third, fourth and fifth deployable regions, respectively) are different from each other, where $A_{f1} < A_{f2} < A_{f3} < A_{f4} < A_{f5}$. The endovascular device 100 comprises a fully deployed configuration after being heated to a temperature at or above $A_{f5}$, which is the highest of the local austenite finish temperatures in this example.

As generally understood by those skilled in the art, austenite start temperature ($A_s$) refers to the temperature at which a phase transformation to austenite begins upon heating for a nickel-titanium shape memory alloy, and austenite finish temperature ($A_f$) refers to the temperature at which the phase transformation to austenite concludes. Martensite start temperature ($M_s$) refers to the temperature at which a phase transformation to martensite begins upon cooling for a nickel-titanium shape memory alloy, and martensite finish temperature ($M_f$) refers to the temperature at which the phase transformation to martensite concludes. Where the adjective "local" appears in front of one of these terms, e.g., "local austenite start [finish] temperature," the term may be understood to refer to the temperature at which the phase transformation begins [concludes] for the nickel-titanium shape memory alloy in only a localized or discrete region of the structural element, such as a discrete region (deployable region) spanning the width or diameter of the element and extending 1 mm or less in length. The size of the discrete region may depend on the spot size of the concentrated heat source (e.g., laser) employed during heat setting of the Nitinol structural element 102, as described below.

Referring again to FIG. 1, as the temperature of the structural element 102 is increased during the gradual heating to reach the lowest local austenite finish temperature ($A_{f1}$), the corresponding deployable region 110 recovers a pre-set shape (i.e., deploys), while the deployable regions 112,114,116,118 corresponding to the higher local austenite finish temperatures ($A_{f2}$, $A_{f3}$, $A_{f4}$ and $A_{f5}$) remain undeployed. Further increases in the temperature of the element 102 past $A_{f2}$, $A_{f3}$, $A_{f4}$ and ultimately $A_{f5}$ allow for sequenced deployment of the endovascular device 100, as illustrated in FIG. 1. The endovascular device 100 may comprise a stent, filter, cage, fastener, ratchet, anchor, or another device.

In the example of FIG. 1, the Nitinol structural element 102 includes five deployable regions, but generally speaking the Nitinol structural element 102 may have n deployable regions, where n is an integer greater than 1. Each of the n deployable regions comprises a local austenite finish temperature above body temperature, and the local austenite finish temperature of at least one of the n deployable regions is different from the local austenite finish temperature of another of the n deployable regions, such that the endovascular device 100 is configured for sequenced deployment within a body vessel. As described above, the Nitinol structural element 102 comprises a fully deployed configuration after being heated to a temperature at or above a highest of the local austenite finish temperatures.

The local austenite finish temperature of the $i^{th}$ deployable region may be represented by $A_{fi}$, where $1 \leq i \leq n$ and n is a positive integer. In some embodiments, all of the n deployable regions may have different local austenite finish temperatures, $A_{f1} \neq A_{f2} \neq \ldots \neq A_{fn}$, as in the example described above. Each of the n deployable regions may further have a local austenite start temperature above body temperature to prevent deployment from initiating prematurely, and the local austenite start temperature of at least one of the n deployable regions may be different from the local austenite start temperature of another of the deployable regions. The local austenite start temperature of the $i^{th}$ deployable region may be represented by $A_{si}$, where $1 \leq i \leq n$ and n is a positive integer. In some embodiments, all of the n deployable regions may have different local austenite start temperatures, $A_{s1} \neq A_{s2} \neq \ldots \neq A_{sn}$.

Thus, generally speaking, a method of sequenced deployment of an endovascular device entails delivering a Nitinol structural element 102 into a body vessel, where the Nitinol structural element 102 comprises n deployable regions (n being an integer greater than 1). Each of the n deployable regions has a local austenite finish temperature above body temperature, and the local austenite finish temperature of at least one of the n deployable regions is different from the local austenite finish temperature of another of the n deployable regions. It is the difference(s) in the local austenite finish temperatures that allows for the sequenced deployment of the endovascular device 100. The local austenite finish temperature of the $i^{th}$ deployable region may be represented by $A_{fi}$, where $1 \leq i \leq n$, as set forth above. The local austenite finish temperatures may fall in a range from 37° C.$<A_{fi} \leq T_{max}$, where $T_{max}$ is below a temperature that may be harmful to body tissue. For example, $T_{max}$ may be 60° C. or lower.

Each of the n deployable regions may also have a local austenite start temperature above body temperature, where the local austenite start temperature of the $i^{th}$ deployable region may be represented by $A_{si}$, where $1 \leq i \leq n$. This ensures that deployment of the endovascular device 100 does not begin prematurely upon delivery of the element 102 into the body vessel. The local austenite start temperature of at least one of the n deployable regions may further be different from the local austenite start temperature of another of the n deployable regions to ensure that initiation of deployment of the device 100 occurs in a sequenced manner.

It is assumed that the Nitinol structural element 102, once placed in the body vessel, attains a temperature up to but not exceeding about 37° C., which is human body temperature. After placement in the vessel, the Nitinol structural element 102 is heated above body temperature, preferably in a controlled manner (e.g., at a specified heating rate) in order to effect deployment. Typically, the heating begins only after the structural element 102 has reached a predetermined site in the body vessel, but in some cases controlled heating may begin prior to this, e.g., during delivery. Each of the n deployable regions exhibits shape recovery to a pre-set shape when the local austenite finish temperature thereof is reached. During the heating, the temperature of the element 102 is gradually increased to at least as high as the highest local austenite finish temperature of the n deployable regions. Thus, a fully deployed configuration of the endovascular device 100 may be achieved in a sequenced manner. The heating preferably occurs uniformly along a length of the Nitinol element 102 during deployment. For example, the temperature along the length of the element 102 may be uniform to within ±1° C. during the heating. The heating may be carried out by an external (ex vivo) or internal heat source, such as an induction or resistive heating mechanism.

Generally speaking, the $i^{th}$ deployable region is fully deployed when the temperature reaches $A_{fi}$. As indicated above, at least one (or some or all) of the n deployable regions has (have) a local austenite finish temperature different from another of the n deployable regions. In one example, the local austenite finish temperature $A_{fj}$ corresponding to the $j^{th}$ deployable region may be higher than $A_{fi}$. The $i^{th}$ and $j^{th}$ regions may be, but do not need to be, adjacent to each other along the element. Accordingly, the $j^{th}$ deployable region does not deploy when the $i^{th}$ deployable region deploys. Instead, the $j^{th}$ deployable region fully deploys after deployment of the $i^{th}$ deployable region and only when the temperature reaches $A_{fj}$ during the gradual heating. Similarly, the $k^{th}$ deployable region may have a local austenite finish temperature $A_{fk}$ that is higher than $A_{fj}$ and $A_{fi}$. Thus, the $k^{th}$ deployable region does not deploy when the $i^{th}$ and $j^{th}$ deployable regions deploy. Instead, the $k^{th}$ deployable region fully deploys only when the temperature reaches $A_{fk}$ during the gradual heating. In another example, $A_{fk}$ of the $k^{th}$ deployable region may be equal to $A_{fj}$ or $A_{fi}$. In such a case, the $k^{th}$ deployable region fully deploys when the temperature reaches $A_{fj}$ or $A_{fi}$ during the gradual heating; in other words, the $k^{th}$ deployable region may be fully deployed at the same time as the $j^{th}$ or $i^{th}$ deployable region. The heating is continued until all of the n deployable regions are fully deployed, thereby forming, in a sequenced deployment process, a deployed configuration of the endovascular device 100. As illustrated in the example of FIG. 1, the $n^{th}$ (e.g., fifth) deployable region, which may comprise an end of the Nitinol structural element 102, may deploy to a fixed configuration in which the end is secured (e.g., by winding) to a midsection or another region of the Nitinol structural element 102.

In order to maintain the deployed configuration of the endovascular device 100 after completion of the gradual heating (e.g., when the device has cooled to body temperature), it may be beneficial to ensure that the martensite start temperature of the Nitinol structural element 102 is below body temperature. With a martensite start temperature below body temperature, the shape memory alloy may remain austenitic (and thus in the deployed configuration) while deployed in the body, even after the heating is stopped. The martensite start temperature may also be selected to be below lower than body temperature, such as below room (ambient) temperature.

Figure 2:
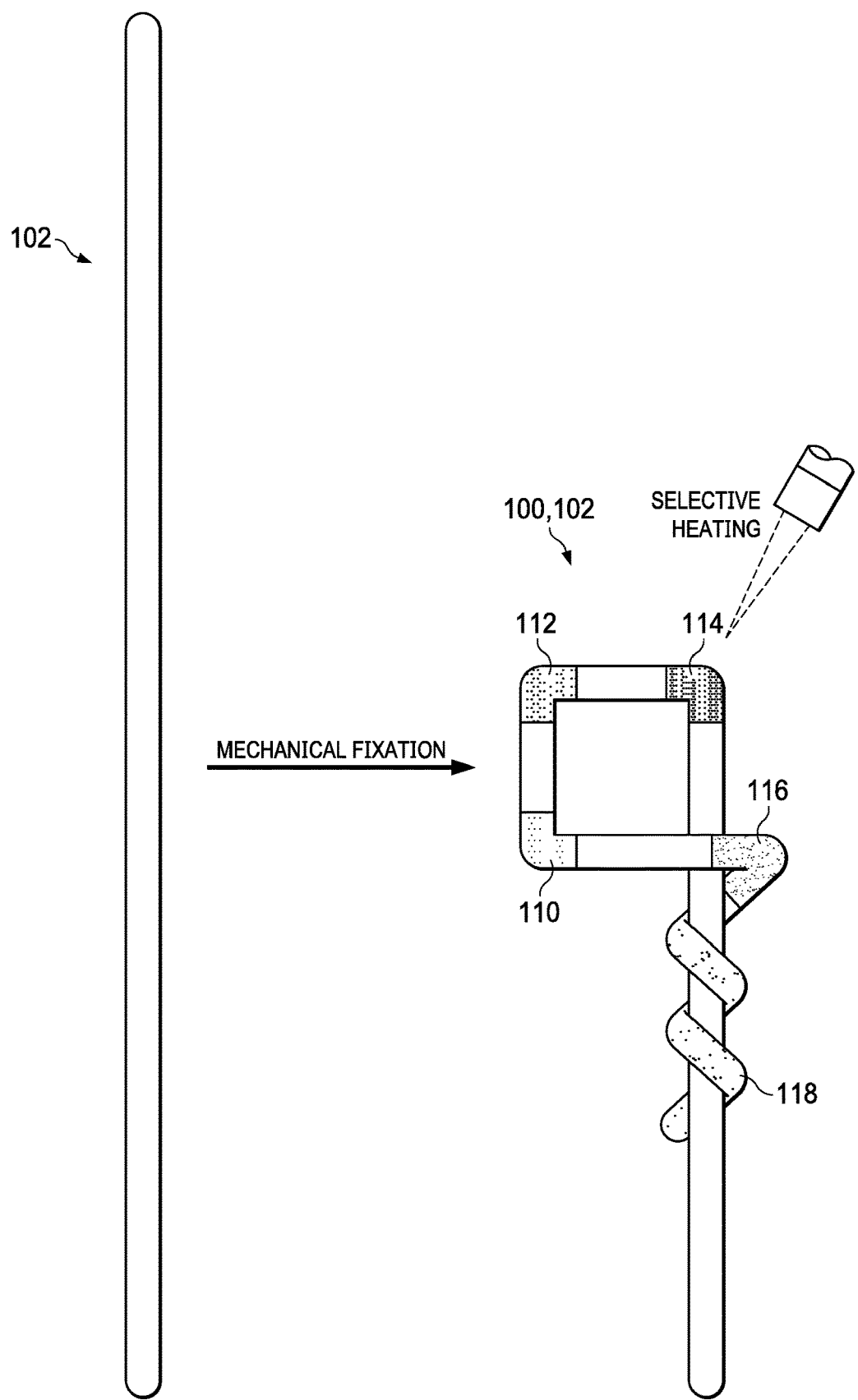
FIG. 2 shows a Nitinol structural element prior to a heat-setting treatment (left schematic) and after being fixed in a predetermined configuration for the heat setting treatment (right schematic), which entails selective heating of n=5 discrete regions of the Nitinol structural element to set the local austenite finish temperatures and form the exemplary endovascular device shown in FIG. 1.

A method of heat setting an endovascular device for sequenced deployment in a body vessel is set forth below in reference to FIG. 2, which shows a Nitinol structural element 102 before and after being mechanically fixed in a predetermined configuration (e.g., by securing to a mandrel).

While the Nitinol structural element 102 is fixed in the predetermined configuration, each of n discrete regions of the element 102 is selectively heated (or "selectively heat set") to impart a pre-set shape. In this example, n=5. The selective heating may be carried out using a concentrated heat source, such as a laser, or by placing each of the n discrete regions between two electrodes connected to a power source. The selective heating may occur at a temperature ("heat setting temperature") and over a time duration sufficient to induce the Nitinol structural element to adopt a "memory" of the predetermined configuration and a local austenite finish temperature above body temperature in each of the n discrete regions. Different temperatures and/or time durations may be employed for the selective heating of different discrete regions. The selective heating may be carried out serially or simultaneously using one or multiple concentrated heat sources. As a consequence of the selective heating, the local austenite finish temperature of at least one of the n discrete regions is different from the local austenite finish temperature of another of the n discrete regions, such that the endovascular device 100 is configured for sequenced deployment within a body vessel, with the n discrete regions serving as n deployable regions 110,112,114,116,118. The $i^{th}$ discrete (deployable) region may have an austenite finish temperature $A_{fi}$, where 1≤i≤n and n is an integer, as discussed above.

It is recognized that the phase transformation temperatures of a nickel-titanium alloy, such as the austenite finish temperature, may be manipulated by altering the level of dislocations and/or the nickel content in solid solution, that is, the amount of nickel present in the matrix of the nickel-titanium alloy. The nickel content of the matrix may be controlled by either vaporization or traditional precipitation of nickel using a suitable heat treatment. Both the temperature and the duration of the heat treatment (e.g., heat setting), may influence the nickel content of the matrix.

Typically, heat setting temperatures from about 350° C. to about 550° C. are employed for the heating. Higher (or lower) temperatures within this temperature range and/or longer (or shorter) heat setting time durations may be used to increase or decrease the phase transformation temperatures. Guidance may be provided by a time-temperature-transformation (TTT) diagram for Nitinol, such as that set forth in Drexel et al., "The Effects of Cold Work and Heat Treatment on the Properties of Nitinol Wire," ASME 2007, $2^{nd}$ Frontiers in Biomedical Devices Conference.

After the predetermined time duration, the heating may be ceased and the Nitinol structural element may optionally be exposed to a cooling fluid (e.g., water) to rapidly quench the temperature. As a consequence of the selective heating, the Nitinol structural element may have, in addition to the local austenite finish temperatures described above, a local austenite start temperature above body temperature in each of the n discrete regions. In addition, the local austenite start temperature of at least one of the n discrete regions may be different from the local austenite start temperature of another of the discrete regions. The $i^{th}$ discrete (deployable) region may have an austenite start temperature $A_{si}$, where 1≤i≤n and n is an integer. In some embodiments, all of the n discrete regions may have different local austenite start temperatures, where $A_{s1} \neq A_{s2} \neq \ldots \neq A_{sn}$. Also or alternatively, all of the n discrete regions may have different local austenite finish temperatures, where $A_{f1} \neq A_{f2} \neq \ldots \neq A_{fn}$, as discussed above.

After the heat setting process, the Nitinol structural element 102 may be deformed (e.g., straightened) into a delivery configuration for introduction into a body vessel. The deformation into the delivery configuration may occur while the shape memory alloy is in the martensitic phase. For example, the Nitinol structural element 102 may be cooled to a temperature at or below the martensite finish temperature, and the element 102 may be readily deformed to the desired delivery configuration. The Nitinol structural element 102 may remain in the delivery configuration until heated to a temperature at or above the lowest local austenite start temperature of the element 102, at which point deployment of the endovascular device 100 may be initiated. Above the lowest local austenite finish temperature of the element 102, full deployment or shape recovery of one (or more) of the discrete regions can occur. As explained above, the endoluminal medical device 100 fully deploys once heated at or above the highest local austenite finish temperature, concluding the sequential deployment process.

Nitinol structural elements (e.g., wire, rod, tubing, strip) 102 suitable for use in the present method may be obtained commercially from any of various vendors or fabricated from a nickel-titanium alloy ingot or billet of a suitable composition using mechanical working (e.g., hot extrusion, cold drawing) and annealing methods known in the art. The nickel-titanium alloy is typically equiatomic or near-equiatomic in composition. For example, the nickel-titanium alloy may comprise from about 50 at. % Ni to about 52 at. % Ni, and titanium and any incidental impurities may account for the balance of the nickel-titanium alloy. In some cases, the nickel-titanium alloy may also include a small amount of an additional alloying element (AAE) (e.g., from about 0.1 at. % AAE to about 10 at. % AAE) to enhance the superelastic or other properties of the nickel-titanium alloy. The additional alloying element may be selected from among B, Al, Cr, Mn, Fe, Co, Cu, Zn, Ga, Ge, Zr, Nb, Mo, Tc, Ru, Rh, Pd, Ag, Cd, In, Sn, Sb, Hf, Ta, W, Re, Os, Ir, Pt, Au, Hg, Tl, Pb, Bi, Po, V, and Mischmetal.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. An endovascular device configured for sequenced deployment in a body vessel, the endovascular device comprising:
   a monolithic Nitinol structural element having n deployable regions, where n is an integer greater than 1, each of the n deployable regions comprising a local austenite finish temperature above body temperature,
   wherein the local austenite finish temperature of at least one of the n deployable regions is different from the local austenite finish temperature of another of the n deployable regions, the endovascular device thereby being configured for sequenced deployment within a body vessel.

2. The endovascular device of claim 1, wherein the monolithic Nitinol structural element comprises a fully deployed configuration after being heated to a temperature at or above a highest of the local austenite finish temperatures.

3. The endovascular device of claim 1, wherein the local austenite finish temperature of an $i^{th}$ deployable region is represented by $A_{fi}$, where $1 \leq i \leq n$ and n is a positive integer, and
   wherein all of the n deployable regions have different local austenite finish temperatures, $A_{f1} \neq A_{f2} \neq \ldots \neq A_{fn}$.

4. The endovascular device of claim 1, wherein each of the n deployable regions further comprises a local austenite start temperature above body temperature, and
   wherein the local austenite start temperature of at least one of the n deployable regions is different from the local austenite start temperature of another of the deployable regions.

5. The endovascular device of claim 4, wherein the local austenite start temperature of an $i^{th}$ deployable region is represented by $A_{si}$, where $1 \leq i \leq n$ and n is a positive integer, and
   wherein all of the n deployable regions have different local austenite start temperatures, $A_{s1} \neq A_{s2} \neq \ldots \neq A_{sn}$.

6. The endovascular device of claim 1, wherein the monolithic Nitinol structural element comprises from about 50 at. % to about 52 at. % nickel.

7. The endovascular device of claim 1 comprising a stent, filter, cage, fastener, ratchet or anchor.

8. A method of sequenced deployment of an endovascular device, the method comprising:
   delivering an endovascular device comprising a monolithic Nitinol structural element into a body vessel, the Nitinol structural element comprising n deployable regions each having a local austenite finish temperature above body temperature, the local austenite finish temperature of at least one of the n deployable regions being different from the local austenite finish temperature of another of the n deployable regions; and
   heating the Nitinol structural element above body temperature,
   wherein each of the n deployable regions is deployed when the local austenite finish temperature thereof is reached, thereby achieving a deployed configuration of the endovascular device in a sequenced deployment process.

9. The method of claim 8, wherein the local austenite finish temperature of an $i^{th}$ deployable region is represented by $A_{fi}$, where $1 \leq i \leq n$ and n is a positive integer, the $i^{th}$ deployable region being deployed when the temperature reaches $A_{fi}$, and
   wherein all of the n deployable regions have different local austenite finish temperatures, $A_{f1} \neq A_{f2} \neq \ldots \neq A_{fn}$.

10. The method of claim 8, wherein the heating is carried out uniformly along a length of the monolithic Nitinol structural element, the temperature of the Nitinol structural element being uniform to within ±1° C.

11. The method of claim 8, wherein the heating is carried out by a heat source selected from the group consisting of: induction heater and resistive heater.

12. The method of claim 8, wherein the $n^{th}$ deployable region deploys to a fixed configuration where the $n^{th}$ deployable region is attached to another portion of the Nitinol structural element.

13. The method of claim 8, wherein a martensite start temperature of the Nitinol structural element is below body temperature, the deployed configuration remaining stable upon cooling after completion of the heating.

14. The method of claim 8, wherein the Nitinol structural element comprises a wire, rod, tube, or strip, and
   wherein the endovascular device comprises a stent, filter, cage, fastener, ratchet or anchor.

15. An endovascular device configured for sequenced deployment in a body vessel, the endovascular device comprising:
   a Nitinol structural element having n deployable regions, where n is an integer greater than 2, each of the n deployable regions comprising a local austenite finish temperature above body temperature,
   wherein the local austenite finish temperature of at least one of the n deployable regions is different from the local austenite finish temperature of another of the n deployable regions, the endovascular device thereby being configured for sequenced deployment within a body vessel.

\* \* \* \* \*